United States Patent
O'Brien et al.

(10) Patent No.: US 7,162,308 B2
(45) Date of Patent: Jan. 9, 2007

(54) NANOTUBE COATINGS FOR IMPLANTABLE ELECTRODES

(75) Inventors: Robert C. O'Brien, Sykesville, MD (US); Christine Frysz, Columbia, MD (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 55 days.

(21) Appl. No.: 10/719,632

(22) Filed: Nov. 21, 2003

(65) Prior Publication Data

US 2005/0075708 A1    Apr. 7, 2005

Related U.S. Application Data

(60) Provisional application No. 60/429,471, filed on Nov. 26, 2002.

(51) Int. Cl.
*A61N 1/00* (2006.01)

(52) U.S. Cl. ..................................... 607/116
(58) Field of Classification Search ............... 607/116, 607/121, 122; 977/DIG. 1
See application file for complete search history.

(56) References Cited

U.S. PATENT DOCUMENTS

| | | | |
|---|---|---|---|
| 3,722,005 A * | 3/1973 | Cowland ..................... | 623/25 |
| 3,783,868 A | 1/1974 | Bokros | |
| 4,281,668 A * | 8/1981 | Richter et al. .............. | 607/121 |
| 4,495,039 A | 1/1985 | Cerise et al. | |
| 4,542,752 A | 9/1985 | DeHaan et al. | |
| 4,602,637 A | 7/1986 | Elmquist et al. | |
| 4,603,704 A | 8/1986 | Mund et al. | |
| 4,612,100 A | 9/1986 | Edeling et al. | |
| 4,784,159 A | 11/1988 | Szilagyi | |
| 4,784,160 A | 11/1988 | Szilagyi | |
| 4,919,135 A | 4/1990 | Phillips, Jr. et al. | |
| 5,338,430 A * | 8/1994 | Parsonage et al. .......... | 204/412 |
| 5,370,684 A | 12/1994 | Vallana et al. | |
| 5,387,247 A | 2/1995 | Vallana et al. | |
| 5,587,200 A * | 12/1996 | Lorenz et al. ............. | 427/2.24 |
| 5,609,611 A | 3/1997 | Bolz et al. | |
| 5,632,770 A | 5/1997 | Schaldach | |
| 5,872,422 A | 2/1999 | Xu et al. | |
| 5,876,454 A * | 3/1999 | Nanci et al. ................ | 424/423 |
| 5,964,794 A | 10/1999 | Bolz et al. | |
| 5,973,444 A | 10/1999 | Xu et al. | |
| 6,048,328 A | 4/2000 | Haller et al. | |
| 6,143,412 A * | 11/2000 | Schueller et al. .......... | 428/408 |
| 6,292,704 B1 * | 9/2001 | Malonek et al. ........... | 607/121 |
| 6,755,530 B1 * | 6/2004 | Loftus et al. ............... | 351/246 |
| 2002/0049495 A1 | 4/2002 | Kutryk et al. | |

(Continued)

FOREIGN PATENT DOCUMENTS

EP   0 453 117 A1   10/1991

(Continued)

*Primary Examiner*—George Manuel
(74) *Attorney, Agent, or Firm*—Michael F. Scalise

(57) ABSTRACT

Coatings for implantable electrodes consisting of single- or multi-walled nanotubes, nanotube ropes, carbon whiskers, and a combination of these are described. The nanotubes can be carbon or other conductive nanotube-forming materials such as a carbon-doped boron nitride. The nanotube coatings are grown "in situ" on a catalytic substrate surface from thermal decomposition, or they are bonded to the substrate using a metal or conductive metal oxide thin film binder deposited by means of a metal compound precursor in liquid form. In the latter case, the precursor/nanotube coating is then converted to a pure metal or conductive metal oxide, resulting in the desired surface coating with imbedded nanotubes.

26 Claims, 3 Drawing Sheets

U.S. PATENT DOCUMENTS

| | | |
|---|---|---|
| 2002/0055010 A1 | 5/2002 | Gao et al. |
| 2002/0085968 A1* | 7/2002 | Smalley et al. ............. 422/198 |
| 2002/0117659 A1* | 8/2002 | Lieber et al. ................. 257/14 |
| 2002/0119176 A1 | 8/2002 | Greenberg et al. |
| 2002/0120296 A1 | 8/2002 | Mech et al. |
| 2002/0150684 A1 | 10/2002 | Jayatissa |
| 2002/0165321 A1 | 11/2002 | Wang et al. |
| 2003/0080085 A1 | 5/2003 | Greenberg et al. |
| 2003/0083697 A1 | 5/2003 | Baudino et al. |
| 2003/0091825 A1 | 5/2003 | Shiffler, Jr. et al. |
| 2003/0093107 A1 | 5/2003 | Parsonage et al. |
| 2003/0102099 A1 | 6/2003 | Yadav et al. |
| 2003/0139794 A1 | 7/2003 | Jenney et al. |
| 2003/0153965 A1 | 8/2003 | Supronowicz et al. |
| 2003/0181328 A1 | 9/2003 | Hwang et al. |
| 2004/0023317 A1* | 2/2004 | Motamedi et al. ............ 435/14 |
| 2004/0151835 A1* | 8/2004 | Croci et al. ............. 427/249.1 |
| 2005/0203604 A1* | 9/2005 | Brabec et al. .............. 607/122 |

FOREIGN PATENT DOCUMENTS

| | | |
|---|---|---|
| WO | WO 9940812 A1 * | 8/1999 |
| WO | WO 02/068323 A1 | 9/2002 |
| WO | WO 3049219 A1 * | 6/2003 |

* cited by examiner

NANOTUBE COATINGS FOR IMPLANTABLE ELECTRODES

CROSS-REFERENCE TO RELATED APPLICATION

The present application claims priority from U.S. provisional application Ser. No. 60/429,471, filed Nov. 26, 2002.

BACKGROUND OF THE INVENTION

1. Field of the Invention

This invention generally relates to coatings for implantable electrodes such as pacing electrodes, neurostimulator electrodes, and electroporating electrodes and sensing electrodes. The three overriding requirements for these types of electrodes are biocompatibility, biostability, and low energy loss. Broadly, the biocompatibility requirement is met if contact of the electrode with body tissue and blood results in little or no immune response from the body, especially thrombogenicity (clotting) and encapsulation of the electrode with fibrotic tissue. The biostability requirement means that all physical, electrical, and chemical properties of the electrode/coating system remain constant and unchanged over the life of the patient. The low energy loss requirement is met if electrode polarization is a minimum.

2. Prior Art

U.S. Pat. No. 4,602,637 to Elmqvist describes a commonly used pacing electrode having sputtered columnar titanium nitride as a coating material. This form of titanium nitride has good conductivity combined with a high specific surface area, resulting in favorable polarization and sensing properties. The disadvantage of titanium nitride, however, is that it degrades the electrical properties of surrounding tissue after implantation. This occurs as the body tissue encapsulates the columnar titanium nitride in fibrotic tissue, which has a lower conductivity than normal tissue.

In the case of a pacing electrode, fibrotic tissue raises the stimulation threshold. The stimulation threshold is the minimum energy required to produce a cardiac contraction. This, in turn, impacts the battery life of the system so that the medical device must be explanted sooner than desired. The encapsulation process also interferes with sensing of intrinsic milivolt signals required by pacemakers. In prior electrode designs, the fibrotic encapsulation problem has been addressed by incorporating a means of metering or eluting steroidal medication to the site of tissue contact over time. However, eluting a steroidal medication to the implant site is not completely effective in eliminating the stimulation threshold rise due to encapsulation. Steroidal medication eluting arrangements have a short duration of effectiveness, and also add cost and complexity to the system, add the risk of infection, and, in many cases, a portion of the electrode working surface must be dedicated to the medication administering function.

Other efforts to overcome the problem of fibrotic encapsulation are described in U.S. Pat. No. 4,495,039 to Cerise et al. and U.S. Pat. No. 4,612,100 to Edeling et al. The former patent relates to electrodes made of pyrolytic carbon while the latter is directed to electrodes coated with amorphous sputtered carbon. These designs meet the requirement of improved biocompatibility, but they do not have the high specific surface characteristics of columnar titanium nitride, and so fall short in polarization and sensing properties.

SUMMARY OF THE INVENTION

The present coating consists of a substrate surface layer comprised of conductive carbonaceous nanotubes or nanotubes of other biocompatible, conductive material. The nanotubes are in the form of single-wall nanotubes (below about 2 nanometers in diameter), multiwall nanotubes (structure of concentric tubes), nanotube ropes, carbon whiskers, and a combination thereof. Multiwall nanotubes are nanotubes grown concentrically. Nanotube ropes consist of a multitude of single- or multi-walled nanotubes bundled in parallel until the diameter increases, typically to about 10 nm to about 100 nm. Nanotube ropes originate at the substrate and grow outward. They can grow into a parallel, close-packed morphology, or into a tangled "hairy" morphology. In either case, the result is a layer consisting of a multitude of nanotubes, each attached at one or both ends to the substrate. The nanotubes can be carbonaceous, or of other conductive and biocompatible nanotube-forming materials, such as carbon-doped boron nitride.

The resulting electrode is both biocompatible and biostable because the nanotube coating is covalently bonded to the electrode surface. Advantageously, the electrode exhibits relatively low polarization because of the greatly increased surface area imparted by the nanotubes. In that respect, the nanotube coating mimics the physical structure of the conventional sputter coated columnar titanium nitride. However, the excellent biocompatibility of nanotube coatings advantageously lessens or eliminates the requirement for a means of providing steroidal medication to the tissue surrounding the electrode.

These and other aspects of the present invention will become increasingly apparent to those skilled in the art by reference to the following description and to the appended drawings.

DETAILED DESCRIPTION OF THE PREFERRED EMBODIMENTS

Figure 1:
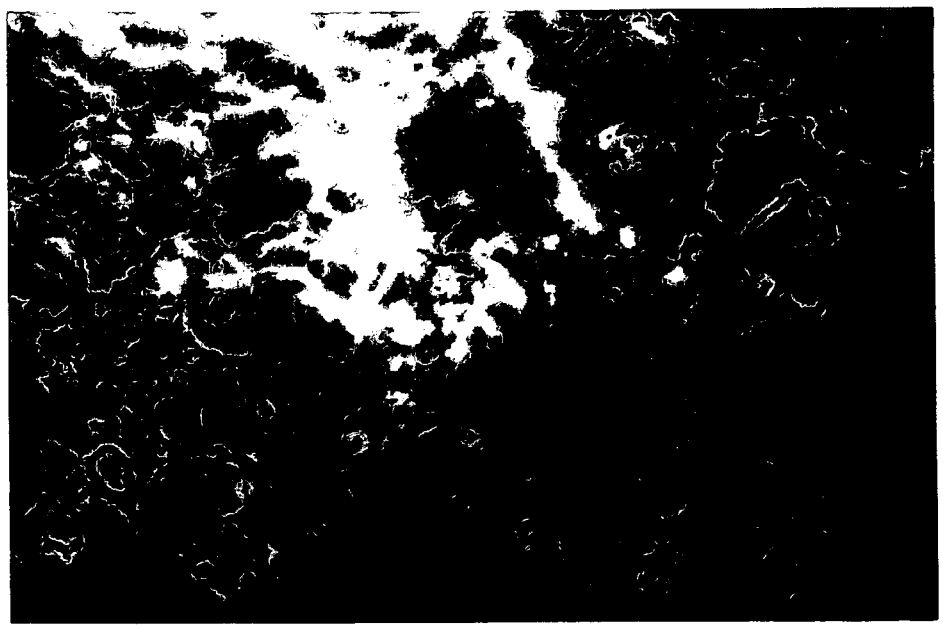
FIG. 1 is a photograph of nanotube ropes grown on a titanium substrate from acetylene at 650° C. at 100,000× magnification.

One preferred embodiment for making a nanotube-coated electrode is by high temperature hydrocarbon decomposition on a substrate. The substrate material must be biocompatible, electrically conductive, and capable of nucleating or catalyzing the desired nanotube structures. Preferred substrate materials include tantalum, titanium, zirconium, platinum, iridium, and niobium. A different base material can be used if the substrate is provided with a coating of these metals or with a coating of a nitride, carbide, carbonitride, or oxide of these metals. An example of this is a tantalum coating on a titanium substrate. Both materials are biocompatible, however, titanium is less expensive than tantalum.

Carbon is another preferred catalyst material for growing nanotubes. Preferably, the carbon is in the form of a machined vitreous carbon electrode or as a thin film carbonaceous coating over a machined metal electrode. Sputtering is one preferred method for applying a relatively thin film carbon coating, in which case the coating consists of amorphous carbon. In particular, if the sputtered amorphous carbon is doped with nitrogen, such as by the presence of nitrogen in the sputter process gas, then the resulting film is an effective catalyst for subsequent growth of nanotubes. If nitrogen is provided, it is preferably at a concentration of about 1 to about 57 atomic percent. The advantage of this carbon nanotube/carbon catalyst system is that the electrode-tissue interface is limited to various allotropes of carbon, which are highly biocompatible materials. That is, when the metal substrate is first provided with sputtered amorphous carbon, it is prevented from being exposed to body fluids and body tissue. If the catalyst layer were a biocompatible metal rather than carbon, the porous nanotube layer would allow the metal to be exposed to body fluids and tissue.

U.S. Pat. Nos. 5,872,422 and 5,973,444, both to Xu et al., describe a conventional process for growing a carbon fiber on a metallic substrate, such as for use in a picture tube. However, the present invention has adapted this process for the production of a nanotube-coated electrode. The process begins with a shaped electrode substrate made of or coated with the appropriate catalyst material first being placed in a closed chamber with a flowing hydrogen atmosphere. The chamber is heated to a temperature from about 350° C. to about 1150° C., more preferably from about 550° C. to about 850° C. When the desired temperature is reached, the hydrocarbon flow is started. Hydrocarbons useful for growing nanotubes are gaseous and include acetylene, methyl acetylene-propadiene (MAPP) gas, and a gas from the paraffin series, i.e., methane, ethane, propane, butane, pentane, etc, and mixtures thereof. Additionally, having been bubbled through an ammonium hydroxide solution can provide the hydrocarbon with an ammonia addition. A typical coating formation time is about 5 minutes to about 1 hour, preferably about 15 minutes. Cooling is done in hydrogen. The resulting nanotubes are generally classified as being nanotube ropes.

Plasma assisted chemical vapor deposition is another preferred method for making a nanotube-coated electrode substrate. The plasma assisted CVD process can be performed by microwave excitation, or by other means. This process is preferred because the resulting nanotube arrays are more highly aligned, which is an objective in attempting to mimic a conventional columnar titanium nitride coating.

Figure 2A:
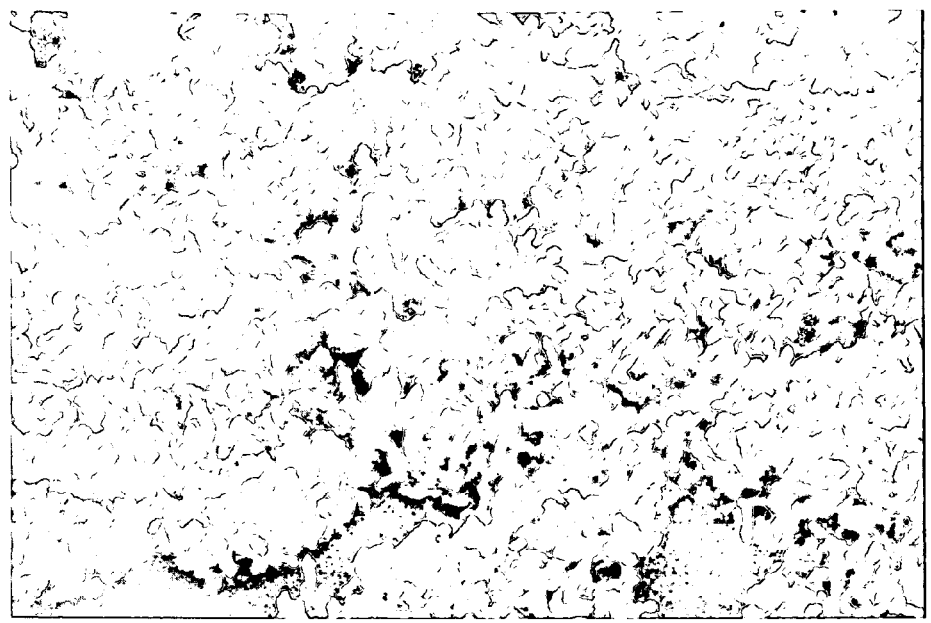
FIGS. 2A and 2B are photographs at 50,000 magnification of nanotube whiskers grown on a titanium substrate from methyl acetylene-propadiene gas bubbled through ammonium hydroxide at 550° C. and 650° C., respectively.
Figure 2B:

The morphology of the nanotubes is partially impacted by the hydrogen source gas. For example, acetylene at about 650° C. gives nanotube ropes about 20 to 50 nm in diameter (FIG. 1). Changing to MAPP gas bubbled through $NH_3OH$ with a heating temperature of about 550° C. results in coarse, more tightly adhering, oriented spiky carbon whiskers (FIGS. 2A and 2B).

Alternatively, bulk loose nanotubes are attached to the electrode surface by means of a thin film binder coating consisting of a biocompatible metal or conductive metal oxide deposited by means of a metal compound precursor in liquid form. The basic method of thin film deposition is described in greater detail in U.S. Pat. No. 4,919,135 to Phillips, which is incorporated herein by reference. Bulk nanotubes are commercially available from numerous sources; for example: Nanostructured and Amorphous Materials, Inc (Los Alamos, N.Mex.). Suitable binder precursors include chloroiridic acid (hydrogen hexachloroiridate IV hydrate), chloroplatinic acid, titanium (IV) chloride, zirconium (IV) chloride, niobium (V) chloride, tantalum (V) chloride, and mixtures thereof. The binder is prepared at room temperature by first dissolving the precursor compound of the biocompatible metal in a solvent. Preferred solvents are alcohols such as tert-butanol, isopropanol, and ethanol.

Loose nanotubes are then mixed into the precursor solution at a high shear rate. The resulting homogeneous mixture is applied to the electrode surface as a thin film by dipping, spraying, doctor blading, by dropper application, or otherwise contacting the metal compound/solvent/nanotube mixture thereto. Solvent removal is by drying the substrate in a warmed atmosphere. This produces a thin metal compound/nanotube layer on the electrode surface. A low temperature heat treatment converts the metal compound layer to a metal/nanotube or metal oxide/nanotube composite thin film. This heating step is carried out at a temperature of about 300° C. to about 500° C. for a time ranging from about 30 minutes to about 3 hours. The resulting thin film has a thickness of about 100 to 500 nanometers, and resembles a porous metal matrix composite with the biocompatible conductive metal oxide or metal as the matrix and the nanotubes being the second phase.

In the case of an iridium oxide binder formed from chloroiridic acid, iridium metal is easily oxidized, and a metal oxide binder results. The preferred converting atmosphere is air. In the case of a binder of platinum, titanium, zirconium, niobium, and tantalum, the respective platinum, titanium, zirconium, niobium, and tantalum metals do not oxidize at the temperatures used. Instead, heating the precursors of these metals in an inert atmosphere, such as of argon, nitrogen, helium, and a vacuum, is expected to result in a metal binder.

The following examples describe the manner and process of a nanotube-coated substrate according to the present invention, and set forth the best mode contemplated by the inventors of carrying out the invention.

EXAMPLE I

Figure 3A:
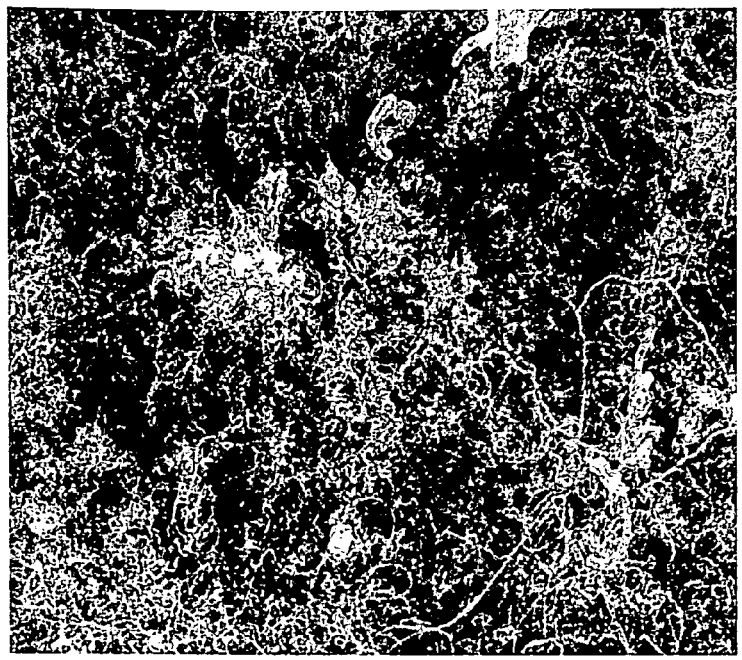
FIGS. 3A and 3B are photographs showing a nanotube coating grown in-situ on a tantalum substrate according to one embodiment of the present invention at magnifications of 20,000× and 50,000×, respectively.
Figure 3B:
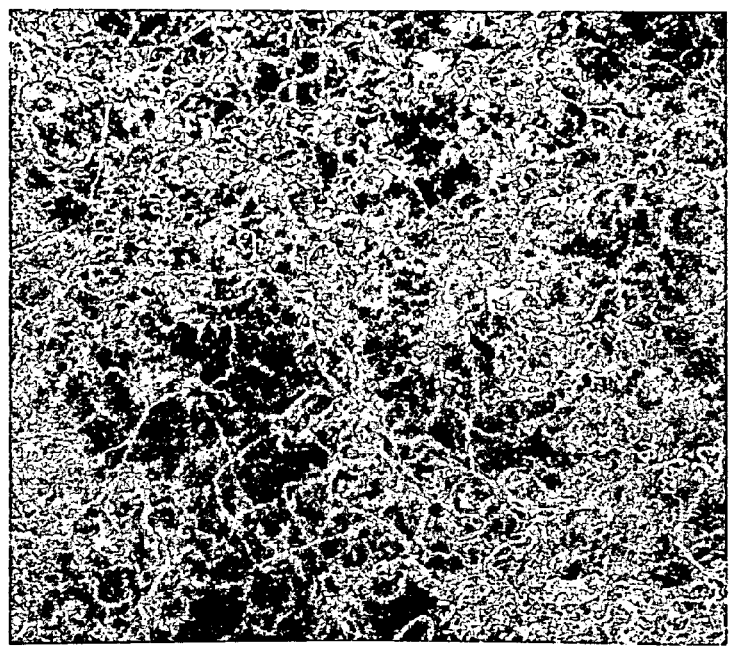

A tantalum substrate was placed in a closed chamber. The chamber was heated to about 650° C. with hydrogen gas flowing through the chamber at a rate of about 1 liter/min. for about every 20 cc of reactive volume. When the reaction chamber reached the desired temperature, 0.5 liter/min of acetylene was added to the reaction gas stream. After about 15 minutes, it was observed that a useable nanotube coating had grown in-situ on the tantalum substrate. The photographs in FIGS. 3A and 3B show the resulting in-situ grown nanotube coating on the tantalum substrate at magnifications of 20,000× and 50,000×, respectively.

A useable nanotube coating can be grown in a similar manner on a substrate of titanium, zirconium, iridium, platinum, niobium, and nitrogen-doped amorphous carbon, or virtually any substrate provided with a thin film coating of these materials. These catalytic or nucleating materials have biocompatible properties similar to those of tantalum.

EXAMPLE II

Etching in aqueous oxalic acid solution at 80° C. for 1 hour cleaned a titanium electrode tip.

A chloroiridic acid solution was prepared by dissolving 1 gram of chloroiridic acid in 35 ml of isopropyl alcohol at room temperature with stirring. Loose nanotube powder was then added while stirring at a high shear rate until a thick, viscous mixture was obtained. The iridium oxide coated substrate was then dipped into the mixture to provide a viscous coating of nanotubes thereon. Heating the coated substrate to about 340° C. in air for about 1 hour converted the metal chloride to iridium metal, which was then subsequently oxidized by further heating. The iridium oxide coated substrate had embedded nanotubes.

Figure 4:
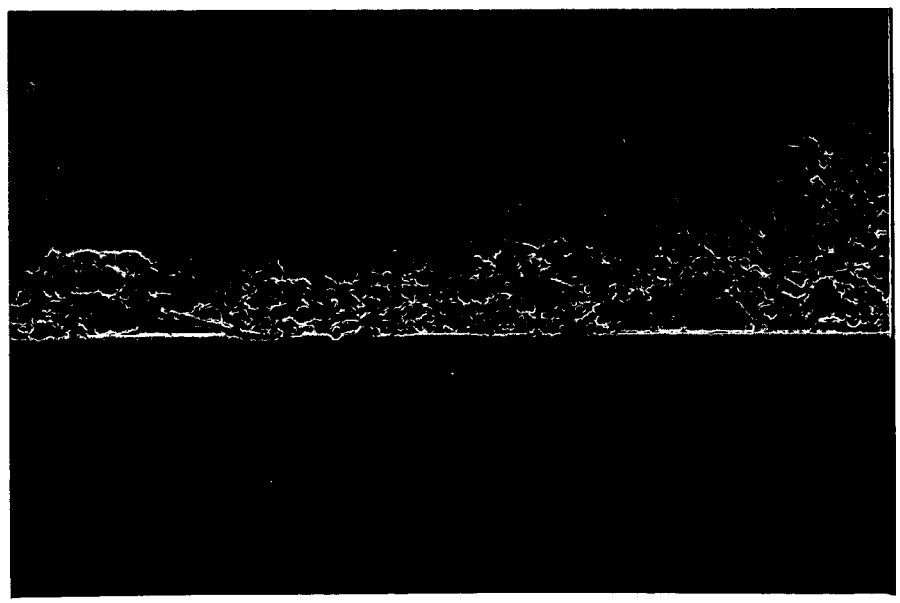
FIG. 4 is a photograph at 20,000× magnification showing a layer of nanotubes bonded to a glass surface using an iridium oxide binder according to another embodiment of the present invention.

The photograph in FIG. 4 shows a similarly generated nanotube coating bonded to a PYREX® glass substrate with iridium oxide binder at a magnification of 20,000×. While the experiment was done with a titanium electrode tip, the reason for the glass substrate was because glass is easily fractured and then viewed edge-on in the SEM in order to image a cross section of the thin film coating. With submicron coatings it is very difficult to get a cross section from the titanium part itself. PYREX® glass was used because it withstands the 340° C. heat treatment without softening or shattering.

It is appreciated that various modifications to the inventive concepts described herein may be apparent to those of ordinary skill in the art without departing from the spirit and scope of the present invention as defined by the appended claims.

What is claimed is:

1. An implantable electrode intended to be imbedded in body tissue, which comprises:
    a) a substrate;
    b) a biocompatible and electrically conductive catalyzing coating supported on the substrate; and
    c) a multiplicity of carbon-containing nanotubes, each comprising a sidewall having a length extending to first and second ends, wherein at least one of the first and second ends is covalently bonded to the coating, the surface portions of the nanotubes that are not covalently bonded exhibiting relatively low polarization with respect to the portions of the nanotubes that are covalently bonded to the coating, wherein with the electrode imbedded in body tissue, electrical energy is transferable through the substrate, the catalyzing coating and then from exposed portions not covalently bonded to the coating of the multiplicity of nanotubes to the body tissue in a low energy loss manner suitable for an implantable electrode.

2. The electrode of claim 1 wherein the substrate is selected from the group consisting of tantalum, titanium, zirconium, iridium, platinum, and niobium.

3. The electrode of claim 1 wherein the substrate is different than the catalyzing coating and the catalyzing coating is selected from the group consisting of tantalum, titanium, zirconium, iridium, platinum, niobium, carbon, and nitrogen-doped carbon.

4. The electrode of claim 3 wherein the nitrogen in the nitrogen-doped carbon is provided at a concentration of about 1 to about 57 atomic percent.

5. The electrode of claim 1 wherein the coating is selected from the group consisting of a nitride, a carbide, a carbonitride, and an oxide of the group of tantalum, titanium, zirconium, iridium, platinum, and niobium.

6. The electrode of claim 1 wherein the nanotubes are in a form selected from the group consisting of single-wall nanotubes, multiwall nanotubes, nanotube ropes, carbon whiskers, and combinations thereof.

7. The electrode of claim 1 wherein the nanotubes are of carbon-doped boron nitride.

8. The electrode of claim 1 wherein the nanotubes are characterized as having been grown from a reaction gas selected from the group consisting of acetylene, methyl acetylene-propadiene, and a gas of the paraffin series.

9. The electrode of claim 8 wherein the reaction gas is characterized as having an ammonium addition.

10. The electrode of claim 1 comprising the nanotubes adhering to tantalum coated on a titanium substrate.

11. A method for providing an implantable electrode, comprising the steps of:
    a) providing a substrate;
    b) coating a catalytic material selected from the group consisting of carbon, nitrogen-doped carbon, tantalum, titanium, zirconium, iridium, platinum, and niobium or a nitride, a carbide, a carbonitride, and an oxide thereof on the substrate;
    c) heating the coated substrate;
    d) contacting the heated substrate with a flowing hydrogen-containing gas stream to thereby provide a multiplicity of carbon-containing nanotubes covalently bonded to the coated substrate, the nanotubes comprising a sidewall having a length extending to first and second ends, wherein at least one of the first and second ends is covalently bonded to the coating, the surface portions of the nanotubes that are not covalently bonded exhibiting relatively low polarization with respect to the portions of the nanotubes that are covalently bonded to the coating; and
    e) wherein with the electrode imbedded in body tissue in a functional manner, electrical energy is transferable through the substrate, the catalyzing coating and then from exposed portions not covalently bonded to the coating of the multiplicity of nanotubes to the body tissue in a low energy loss manner suitable for an implantable electrode.

12. The method of claim 11 including heating the coated substrate to a temperature of about 350° C. to about 1,150° C.

13. The method of claim 11 including cooling the nanotube coated substrate in hydrogen prior to use.

14. A method of providing an implantable electrode, comprising the steps of:
    a) providing a substrate;
    b) providing nanotubes mixed with a binder precursor selected from chloroiridic acid, chloroplatinic acid, titanium (IV) chloride, zirconium (IV) chloride, niobium (V) chloride, and tantalum (V) chloride in a solvent;
    c) contacting the binder precursor to the substrate;
    d) converting the binder precursor to a coating on the substrate having a multiplicity of nanotubes covalently bonded thereto, the nanotubes comprising a sidewall having a length extending to first and second ends, wherein at least one of the first and second ends is covalently bonded to the coating, the surface portions of the nanotubes that are not covalently bonded exhibiting relatively low polarization with respect to the portions of the nanotubes that are covalently bonded to the coating; and
    d) wherein with the electrode imbedded in body tissue in a functional manner, electrical energy is transferable through the substrate, the catalyzing coating and then from exposed portions not covalently bonded to the coating of the multiplicity of nanotubes to the body tissue in a low energy loss manner suitable for an implantable electrode.

15. The method of claim 14 including heating the binder precursor coated substrate in either an oxidizing or an inert atmosphere.

16. The method of claim 14 including heating the binder precursor coated substrate at a temperature of about 300° C. to about 500° C.

17. The method of claim 14 including heating the binder precursor coated substrate for a time ranging from about 30 minutes to about 3 hours.

18. The method of claim 14 including heating the chloroiridic acid binder precursor in an oxidizing atmosphere to provide the nanotubes adhered to an iridium oxide binder coated on the substrate.

19. The method of claim 14 including heating the chloroplatinic acid, titanium (IV) chloride, zirconium (IV) chloride, niobium (V) chloride, and tantalum (V) chloride binder precursors in an inert atmosphere to provide the nanotubes adhered to a binder of platinum, titanium, zirconium, niobium, and tantalum, respectively, coated on the substrate.

20. A method for providing an implantable electrode, comprising the steps of:
   a) providing a substrate;
   b) coating a carbonaceous catalytic material on the substrate;
   c) heating the carbonaceous coated substrate;
   d) contacting the heated substrate with a flowing hydrogen-containing gas stream to thereby provide a multiplicity of carbon-containing nanotubes covalently bonded to the carbonaceous coated substrate, the nanotubes comprising a sidewall having a length extending to first and second ends, wherein at least one of the first and second ends is covalently bonded to the coating, the surface portions of the nanotubes that are not covalently bonded exhibiting relatively low polarization with respect to the portions of the nanotubes that are covalently bonded to the coating; and
   e) wherein with the electrode imbedded in body tissue in a functional manner, electrical energy is transferable transfers through the substrate, the catalyzing coating and then from exposed portions not covalently bonded to the coating of the multiplicity of nanotubes to the body tissue in a low energy loss manner suitable for an implantable electrode.

21. The method of claim 20 including heating the carbonaceous coated substrate to a temperature of about 350° C. to about 1,150° C.

22. The method of claim 20 including sputtering the carbonaceous catalytic material on the substrate.

23. The method of claim 20 including providing the sputtered carbonaceous catalytic material as nitrogen-doped carbon.

24. The method of claim 20 including providing the nitrogen in the nitrogen-doped carbon at a concentration of about 1 to about 57 atomic percent.

25. A method for providing an implantable electrode, comprising the steps of:
   a) providing a substrate;
   b) coating a catalytic material selected from the group consisting of carbon, nitrogen-doped carbon, tantalum, titanium, zirconium, iridium, platinum, and niobium or a nitride, a carbide, a carbonitride, and an oxide thereof on the substrate;
   c) subjecting the coated substrate to a plasma assisted chemical vapor deposition process containing a flowing hydrocarbon-containing gas stream to thereby provide a multiplicity of carbon-containing nanotubes covalently bonded to the coated substrate, the nanotubes comprising a sidewall having a length extending to first and second ends, wherein at least one of the first and second ends is covalently bonded to the coating, the surface portions of the nanotubes that are not covalently bonded exhibiting relatively low polarization with respect to the portions of the nanotubes that are covalently bonded to the coating; and
   d) wherein with the electrode imbedded in body tissue in a functional manner, electrical energy is transferable through the substrate, the catalyzing coating and then from exposed portions not covalently bonded to the coating of the multiplicity of nanotubes to the body tissue in a low energy loss manner suitable for an implantable electrode.

26. The method of claim 25 including utilizing microwave excitation in the plasma assisted chemical vapor deposition process.

* * * * *